United States Patent
Kostrzewski (10) Patent No.: US 9,220,586 B2
(45) Date of Patent: Dec. 29, 2015

(54) SURGICAL IMPLANT AND APPLICATOR

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/023,497

(22) Filed: Sep. 11, 2013

(65) Prior Publication Data

US 2014/0094829 A1   Apr. 3, 2014

Related U.S. Application Data

(60) Provisional application No. 61/706,876, filed on Sep. 28, 2012.

(51) Int. Cl.
*A61F 2/02* (2006.01)
*A61F 2/00* (2006.01)

(52) U.S. Cl.
CPC .............. *A61F 2/0063* (2013.01); *A61F 2/0077* (2013.01); *A61F 2002/0068* (2013.01)

(58) Field of Classification Search
CPC .............. A61B 17/0057; A61B 2017/00575; A61B 2017/00579; A61B 2017/0061; A61F 2/0063; A61F 2002/0072; B44C 6/00; B44C 6/02; B44C 6/06
USPC ............ 156/574, 71, 577, 579; 606/151, 213, 606/215; 623/23.72, 23.73, 23.74; 428/192, 428/198; 225/39
See application file for complete search history.

(56) References Cited

U.S. PATENT DOCUMENTS

| | | | | |
|---|---|---|---|---|
| 3,737,360 A | * | 6/1973 | Horn | 156/577 |
| 4,421,807 A | * | 12/1983 | Clausing et al. | 428/40.3 |
| 5,116,357 A | | 5/1992 | Eberbach | |
| 5,147,387 A | | 9/1992 | Jansen et al. | |
| 5,263,969 A | | 11/1993 | Phillips | |
| 5,304,187 A | | 4/1994 | Green et al. | |
| 5,380,328 A | | 1/1995 | Morgan | |
| 5,403,432 A | * | 4/1995 | Burch | 156/577 |

(Continued)

FOREIGN PATENT DOCUMENTS

| | | |
|---|---|---|
| EP | 2014331 A2 | 1/2009 |
| EP | 2050474 A2 | 4/2009 |

(Continued)

OTHER PUBLICATIONS

European Search Report, Application No. EP 13 18 6538 dated Jan. 13, 2014.

*Primary Examiner* — Todd E Manahan
*Assistant Examiner* — Charles Wei (57) ABSTRACT

A surgical repair device is provided and includes a roll of surgical mesh material and an applicator for applying the roll of surgical mesh material to tissue. The applicator has a generally cylindrical body portion defining a chamber for receipt of the roll of surgical mesh material and longitudinally extending edges defining a gap therebetween for exposing the roll of surgical mesh material to the tissue. The surgical mesh material has a non-adhering surface and an adhering surface for engaging the tissue and securing the surgical mesh to the tissue. The roll of mesh material is oriented within the chamber with the adhering surfacing outward. A method of using the surgical repair device to repair a tear in tissue is also provided.

20 Claims, 6 Drawing Sheets

(56) References Cited

U.S. PATENT DOCUMENTS

| | | |
|---|---|---|
| 5,464,403 A | 11/1995 | Kicturakis et al. |
| 5,695,525 A * | 12/1997 | Mulhauser et al. ............ 606/151 |
| 5,851,348 A * | 12/1998 | Muenzer et al. .............. 156/577 |
| 5,968,096 A * | 10/1999 | Whitson et al. ............... 424/423 |
| 6,478,803 B1 | 11/2002 | Kapec et al. |
| 6,517,584 B1 * | 2/2003 | Lecalve ..................... 623/23.72 |
| 6,695,856 B2 | 2/2004 | Kicturakis et al. |
| 7,846,171 B2 | 12/2010 | Kullas et al. |
| 2002/0173807 A1 * | 11/2002 | Jacobs ........................... 606/151 |
| 2004/0039415 A1 * | 2/2004 | Zamierowski ................ 606/215 |
| 2004/0092970 A1 | 5/2004 | Xavier |
| 2004/0163753 A1 * | 8/2004 | Pederson et al. ................. 156/71 |
| 2005/0021058 A1 | 1/2005 | Negro |
| 2007/0112361 A1 | 5/2007 | Schonholz et al. |
| 2008/0195121 A1 | 8/2008 | Eldar et al. |
| 2009/0204228 A1 * | 8/2009 | Hiles .......................... 623/23.72 |
| 2010/0292718 A1 | 11/2010 | Sholev et al. |
| 2011/0021965 A1 | 1/2011 | Karp et al. |
| 2011/0152896 A1 | 6/2011 | Purvis, Jr. |
| 2011/0282365 A1 * | 11/2011 | Hadba et al. ................... 606/151 |
| 2012/0193388 A1 * | 8/2012 | Machota et al. ................. 225/39 |

FOREIGN PATENT DOCUMENTS

| | | |
|---|---|---|
| WO | WO 96/41588 A1 | 12/1996 |
| WO | WO 9641588 A1 * | 12/1996 |
| WO | 2007056297 A2 | 5/2007 |

* cited by examiner

SURGICAL IMPLANT AND APPLICATOR

CROSS-REFERENCE TO RELATED APPLICATIONS

This application claims the benefit of and priority to U.S. Provisional Patent Application No. 61/706,876, filed Sep. 28, 2012, the entire disclosure of which is incorporated by reference herein.

BACKGROUND

1. Technical Field

The present disclosure relates to a surgical implant and applicator. More particularly, the present disclosure relates to surgical mesh and an applicator for applying the surgical mesh across the surface of tissue.

2. Background of Related Art

Surgical meshes formed from degradable or non-degradable materials for use during both open and minimally invasive surgeries are known. These meshes are typically flat, fibrous material that a surgeon places over a defect, such as a tear in tissue, as reinforcement. The surgeon then secures the mesh in place with a surgical fastener, such as a staple, clip, tack, suture or the like.

This often requires multiple steps including insertion of the mesh into the operative site and positioning the mesh across the tear. Subsequently, a surgical fastener applier is inserted into the operative site to affix the surgical mesh to the tissue.

Thus, it is desirable to provide an applicator for applying surgical mesh to tissue. It is further desirable to provide a surgical repair device having an applicator containing a self-adhering surgical mesh to simultaneously apply and secure the surgical mesh to tissue.

SUMMARY

There is disclosed an applicator for applying a surgical mesh to tissue to repair a tear or puncture the tissue. The applicator generally includes a body portion having an inner surface defining a chamber for receipt of a surgical mesh, an outer surface and first and second longitudinally extending edges. The first and second longitudinal edges define a gap therebetween for passage of the surgical mesh. The body portion is a semi-cylindrical body portion having first and second open ends for receipt of a roll of mesh material. The outer surface of the body portion includes gripping structure for manipulating the body portion relative to tissue.

In one embodiment, the gripping structure includes a finger grip projecting from the outer surface of the body portion. In a specific embodiment, a roller assembly is provided for support of the surgical mesh within the chamber. The roller assembly includes a first end cap attached to the first open end of the body portion and a second end cap attached to the second open end of the body portion. The roller assembly additionally includes a shaft extending between the first and second end caps. A first end of the shaft is affixed to the first end cap and a second end of the shaft is supported within a socket formed in the second end cap.

There is also disclosed a surgical repair device for applying a surgical mesh to tissue to repair a tear or puncture in the tissue. The surgical repair device generally includes a body portion having an inner surface defining a chamber and first and second longitudinal edges defining a gap therebetween and a roll of mesh material positioned within the chamber. The roll of mesh material has a first adhering side and a second non-adhering side. The roll of mesh material is oriented in a reverse roll within the chamber and with the adhering side facing outward such that the adhering side is exposed through the gap defined by the first and second longitudinal edges. In a specific embodiment, the adhering side of the roll of mesh material includes tissue engaging barbs for anchoring the mesh to tissue and the non-adhering side resists puncture from the barbs.

The body portion of the surgical repair device includes gripping structure projecting from an outer surface of the body portion. In a specific embodiment, the body portion is semi-cylindrical.

In a further specific embodiment, the roll of mesh material includes a first length of adhesive material along an edge of the non-adhering side and a second length of adhesive material along an edge of the adhering side.

There is further disclosed a method of applying a surgical mesh to a tear in tissue including providing a surgical repair device having a body portion defining a chamber and first and second longitudinal edges defining a gap therebetween. A roll of mesh material is positioned within the chamber and has a first adhering side exposed through the gap. The first adhering side of the roll of mesh material is exposed to tissue surrounding a tear in the tissue and the body portion of the surgical repair device is dragged across the tissue surrounding tear in tissue to cause the first adhering side of the roll of mesh material to engage the tissue. The roll of mesh material is unrolled as the body portion is dragged across the tissue.

In a more particular method, a second roll of mesh material is unrolled across the tissue such that an edge of the second roll of mesh material overlaps an edge of the unrolled roll of mesh material applied to tissue. The edge of the roll of mesh material includes a first adhesive strip and the second roll of mesh material includes an edge having a second adhesive strip such that the second adhesive strip engages the first adhesive strip in overlapping relation.

DESCRIPTION OF THE DRAWINGS

Various embodiments of the presently disclosed surgical mesh and applicator device are disclosed herein with reference to the drawings, wherein.

DETAILED DESCRIPTION OF EMBODIMENTS

Embodiments of the presently disclosed surgical mesh and applicator will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user. As used herein the term "surgical mesh" is used to refer to any three-dimensional grip-type implant for use in surgical procedures, such as, for example, meshes that do not require suturing to the abdominal wall. Although described herein with reference to a hernia mesh, the method of the disclosure may be used in any surgical repair. As used herein the term "laparoscopic deployment device" is used to refer to a deployment device that may be used during minimally invasive surgeries described above. Although described herein with reference to a minimally invasive surgery, the surgical mesh may also be used in open surgery.

Figure 1:
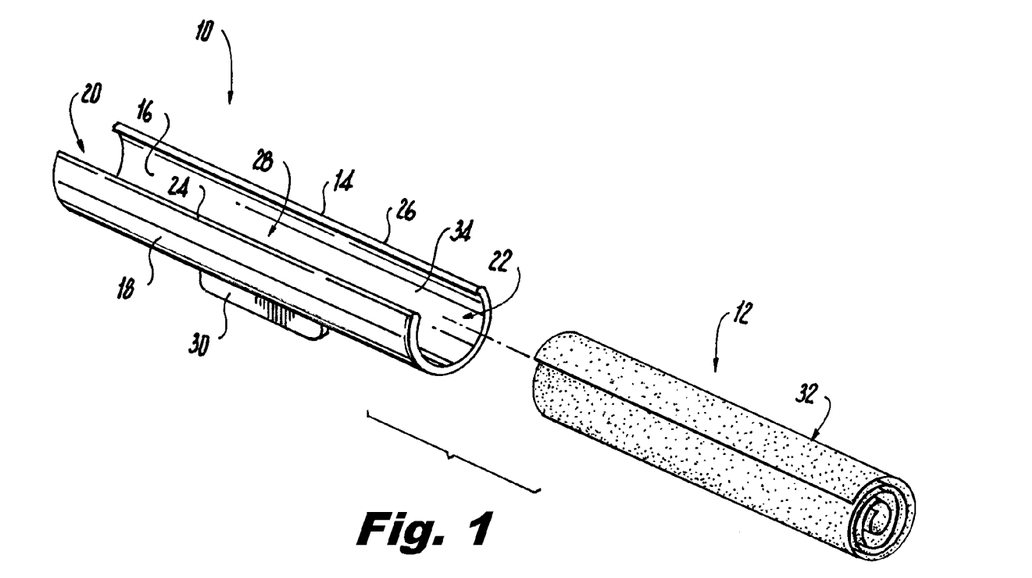
FIG. 1 is a perspective view, with parts separated, of one embodiment of a roll of surgical mesh and an applicator for applying the surgical mesh to tissue.

Referring initially to FIG. 1, there is disclosed one embodiment of an applicator 10 and a surgical mesh 12, positionable within applicator 10, for use in repairing a tear in a body wall of a patient. Applicator 10 generally includes a semi-cylindrical body portion 14 having an inner surface 16, an outer surface 18 and first and second open ends 20 and 22, respectively. Semi-cylindrical body portion is formed with first and second longitudinal edges 24 and 26 which define a gap 28 therebetween for exposing surgical mesh 12 to tissue. A generally rectangular finger grip 30 extends from body portion 14 to facilitate manipulation of applicator 10 relative to tissue. Body portion 14 of applicator 10 can be formed as a flexible structure to loosely grasp or hug surgical mesh 12 or may be a rigid structure. Applicator 10 can be formed from a variety of known biocompatible materials such as, for example, metallic materials, polymeric materials, etc. Surgical mesh 12 is provided as a roll of mesh material 32 which is loosely retained within a chamber 34 defined by inner surface 16 of body portion 14.

Figure 2:
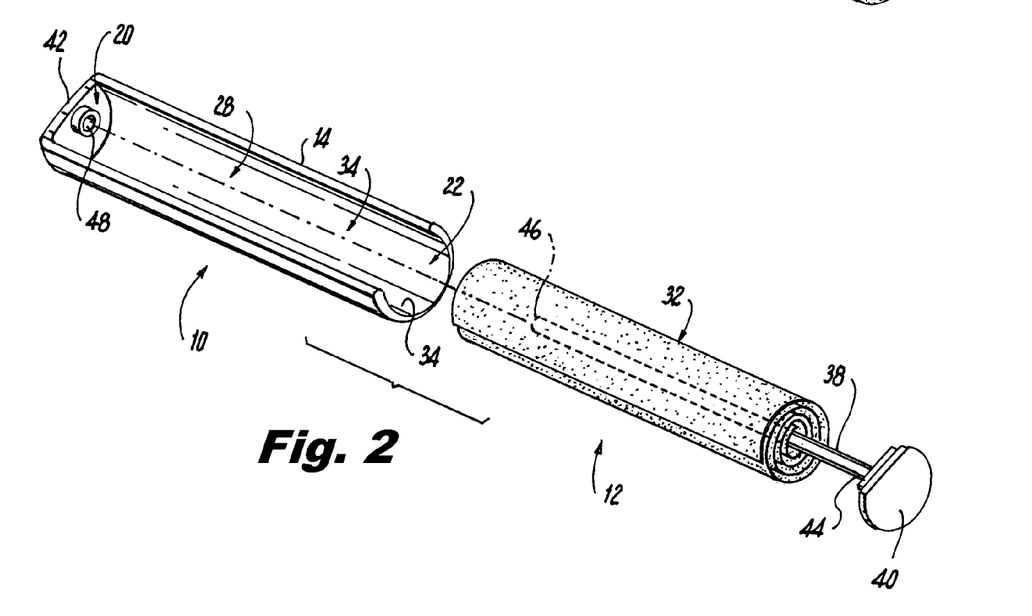
FIG. 2 is a perspective view, with parts separated, of the applicator and surgical mesh of FIG. 1 incorporating a roller assembly for supporting the surgical mesh within the applicator.

Referring to FIG. 2, in one embodiment, a roller assembly 36 is provided to support the roll of mesh material 32 within chamber 34 of body portion 14. Roller assembly 36 includes a shaft 38 for supporting the roll of mesh material 32 and first and second end caps 40 and 42, respectively, for supporting shaft 38 within body portion 14. A first end 44 of shaft 32 is affixed to first end cap 40. Second end cap 42 is affixed to body portion 14 over first open end 20 of body portion 14. Upon assembly, shaft 38 is inserted through the roll of mesh material 32 and first end cap 40 is affixed to second open end 22 of body portion 14 in snap fit fashion. A second end 46 of shaft 38 is removably supported in a socket 48 formed on second end cap 42. In this manner, the roll of mesh material 32 is rotatably retained within chamber 34 of body portion 14 and exposed for dispensing to tissue through gap 28 in body portion 14 in a manner described in more detail hereinbelow.

Figure 3:
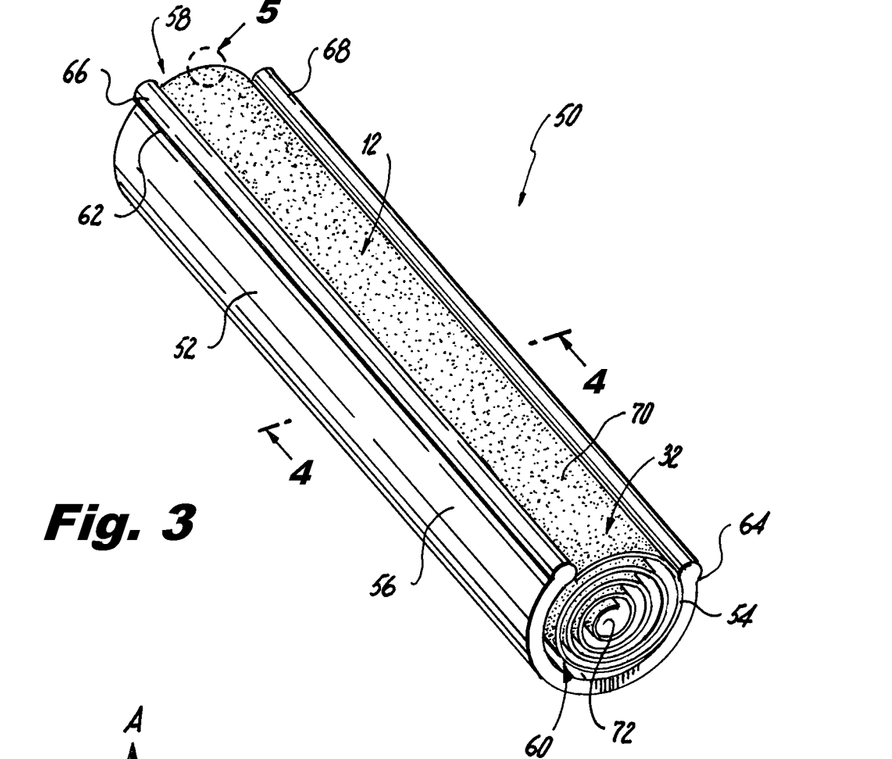
FIG. 3 is a perspective view of an alternative embodiment of an applicator for applying the surgical mesh to tissue.
Figure 4:
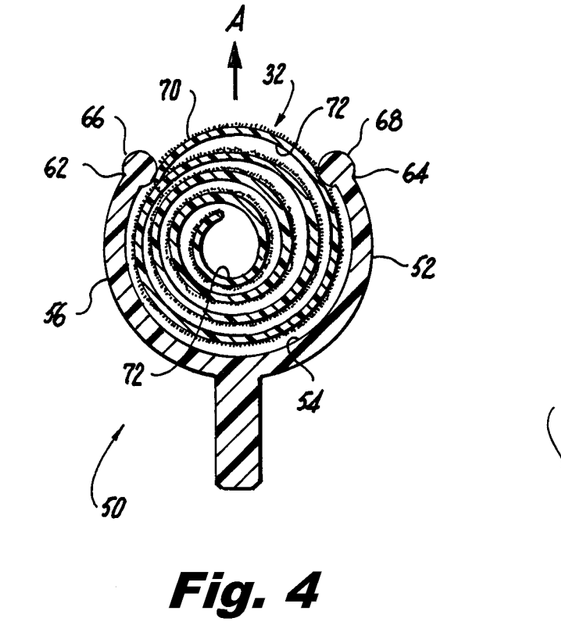
FIG. 4 is a cross-sectional view taken along line 4-4 of FIG. 3.

Referring for the moment to FIGS. 3 and 4, there is disclosed an alternative embodiment of an applicator 50 for use with surgical mesh 12. Like applicator 10 above, applicator 50 has a body portion 52 having an inner surface 54, an outer surface 56, a first open end 58 and a second open end 60. In this embodiment, body portion 52 includes first and second longitudinal edges 62 and 64 which are provided with atraumatic, bulbous surfaces 66 and 68, respectively. Bulbous surfaces 66 and 68 allow applicator 50 to be passed smoothly over tissue and facilitate passage of the roll of mesh material 32 out of applicator 50.

Figure 5:
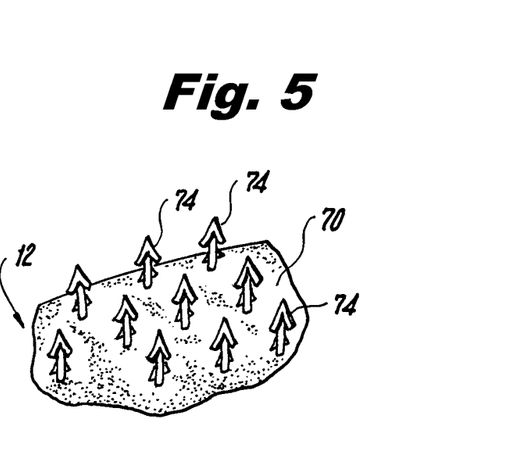
FIG. 5 is an enlarged area of detail view taken from FIG. 3.

With specific reference to FIGS. 3-5, surgical mesh 12 forming the roll of mesh material 32 is formed with a first or tissue adhering surface 70 and a second or non-adhering surface 72. When surgical mesh 12 is manipulated to form the roll of mesh material 12, it is rolled in a "reverse roll" fashion such that adhering surface 70 faces outward, in the direction of arrow A (FIG. 4). Non-adhering surface 72 is formed from a material that will not stick or adhere to itself or tissue to allow surgical mesh 12 to be formed into the roll of mesh material 32 and easily unraveled as it is applied to tissue.

Adhering surface 70 may be formed from a variety of materials. With specific reference to FIG. 5, in this embodiment, adhering surface 70 of surgical mesh 12 is formed with tissue engaging tags or barbs 74 projecting from surgical mesh 12. Barbs 74 are provided to penetrate into tissue and retain surgical mesh 12 in place as it is rolled across tissue. Non-adhering surface 72 is structured to resist penetration by barbs 74 and allow surgical mesh 12 to be placed in the rolled condition without sticking to itself.

Materials

The fibers forming the combination mesh may be made from any fiber-forming biocompatible polymer. The biocompatible polymer may be synthetic or natural. The biocompatible polymer may be biodegradable, non-biodegradable or a combination of biodegradable and non-biodegradable. The term "biodegradable" as used herein is defined to include both bioabsorbable and bioresorbable materials. By biodegradable, it is meant that the materials decompose, or lose structural integrity under body conditions (e.g., enzymatic degradation or hydrolysis) or are broken down (physically or chemically) under physiologic conditions in the body such that the degradation products are excretable or absorbable by the body.

Representative natural biodegradable polymers which may be used include: polysaccharides, such as alginate, dextran, chitin, hyaluronic acid, cellulose, collagen, gelatin, fucans, glycosaminoglycans, and chemical derivatives thereof (substitutions and/or additions of chemical groups, for example, alkyl, alkylene, hydroxylations, oxidations, and other modifications routinely made by those skilled in the art); and proteins, such as albumin, casein, zein, silk, and copolymers and blends thereof, alone or in combination with synthetic polymers.

Synthetically modified natural polymers which may be used include: cellulose derivatives, such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These are collectively referred to herein as "celluloses."

Representative synthetic degradable polymers suitable for use include: polyhydroxy acids prepared from lactone monomers, such as glycolide, lactide, caprolactone, ε-caprolactone, valerolactone, and δ-valerolactone, as well as pluronics, carbonates (e.g., trimethylene carbonate, tetramethylene carbonate, and the like); dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactide-co-(ε-caprolactone-)); poly(glycolide-co-(ε-caprolactone)); polycarbonates; poly(pseudo amino acids); poly(amino acids); poly(hydroxyalkanoate)s; polyalkylene oxalates; polyoxaesters; polyanhydrides; polyortho esters; and copolymers, block copolymers, homopolymers, blends, and combinations thereof.

Some non-limiting examples of suitable non-bioabsorbable materials from which the fibers of the grip-type knit mesh and smaller prosthetic knit mesh may be made include: polyolefins, such as polyethylene and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins, such as fluoroethylenes, fluoropropylenes, fluoroPEGSs, and polytetrafluoroethylene; polyamides, such as nylon and polycaprolactam; polyamines; polyimines; polyesters, such as polyethylene terephthalate and polybutylene terephthalate; aliphatic polyesters; polyethers; polyether-esters, such as polybutester; polytetramethylene ether glycol; 1,4-butanediol; polyurethanes; acrylic polymers and copolymers; modacrylics; vinyl halide polymers and copolymers, such as polyvinyl chloride; polyvinyl alcohols; polyvinyl ethers, such as polyvinyl methyl ether; polyvinylidene halides, such as polyvinylidene fluoride and polyvinylidene chloride; polyacrylonitrile; polyaryletherketones; polyvinyl ketones; polyvinyl aromatics, such as polystyrene; polyvinyl esters, such as polyvinyl acetate; copolymers of vinyl monomers with each other and olefins, such as etheylene-methyl methacrylate copolymers, acrylonitrile-styrene copolymers, ABS resins, and ethylene-vinyl acetate copolymers; alkyd resins; polycarbonates; polyoxymethylenes; polyphosphazine; polyimides; epoxy resins; aramids, rayon; rayon-triacetate; spandex; silicones; and combinations thereof.

Rapidly biodegradable polymers, such as poly(lactide-co-glycolide)s, polyanhydrides, and polyorthoesters, which have carboxylic groups exposed on the external surface as the smooth surface of the polymer erodes, may also be used. It should, of course, be understood that any combination of natural, synthetic, biodegradable, and non-biodegradable materials may be used to form the combination mesh.

In embodiments, the naps of the grip-type knit mesh are formed from polylactic acid (PLA) and the mesh is formed from a monofilament polyester of polyethylene terephthalate (PET). In embodiments, the smaller prosthetic mesh is formed from a polypropylene monofilament.

Bioactive Agents

The grip-type knit mesh and/or the prosthetic knit mesh may include a bioactive agent. The term "bioactive agent" as used herein, is used in its broadest sense and includes any substance or mixture of substances that have clinical use. Consequently, bioactive agents may or may not have pharmacological activity per se, e.g., a dye.

Alternatively, a bioactive agent could be any agent that provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the implant in any suitable form of matter, e.g., films, powders, liquids, gels and the like.

The bioactive agent may be bound to the grip-type knit mesh and/or the smaller prosthetic knit mesh covalently, non-covalently, i.e., electrostatically, through a thiol-mediated or peptide-mediated bond, or using biotin-avidin chemistries and the like.

Examples of classes of bioactive agents, which may be utilized in accordance with the present disclosure include, for example, anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors, and enzymes. It is also intended that combinations of bioactive agents may be used.

Suitable antimicrobial agents which may be included as a bioactive agent include, for example: triclosan, also known as 2,4,4'-trichloro-2'-hydroxydiphenyl ether; chlorhexidine and its salts, including chlorhexidine acetate, chlorhexidine gluconate, chlorhexidine hydrochloride, and chlorhexidine sulfate; silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine; polymyxin, tetracycline, aminoglycosides, such as tobramycin and gentamicin, rifampicin, bacitracin, neomycin; chloramphenicol; miconazole; quinolones such as oxolinic acid, norfloxacin, nalidixic acid, pefloxacin, enoxacin and ciprofloxacin; penicillins such as oxacillin and pipracil; nonoxynol 9; fusidic acid; cephalosporins; and combinations thereof. In addition, antimicrobial proteins and peptides such as bovine lactoferrin and lactoferricin B may be included as a bioactive agent.

Other bioactive agents which may be included are: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; antispasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents which may be included in the grip-type knit mesh and/or the smaller prosthetic knit mesh include, for example, viruses and cells, including stem cells; peptides, polypeptides and proteins, as well as analogs, muteins, and active fragments thereof immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids, such as antisense molecules, DNA, RNA, RNAi; oligonucleotides; polynucleotides; and ribozymes.

Figure 6:
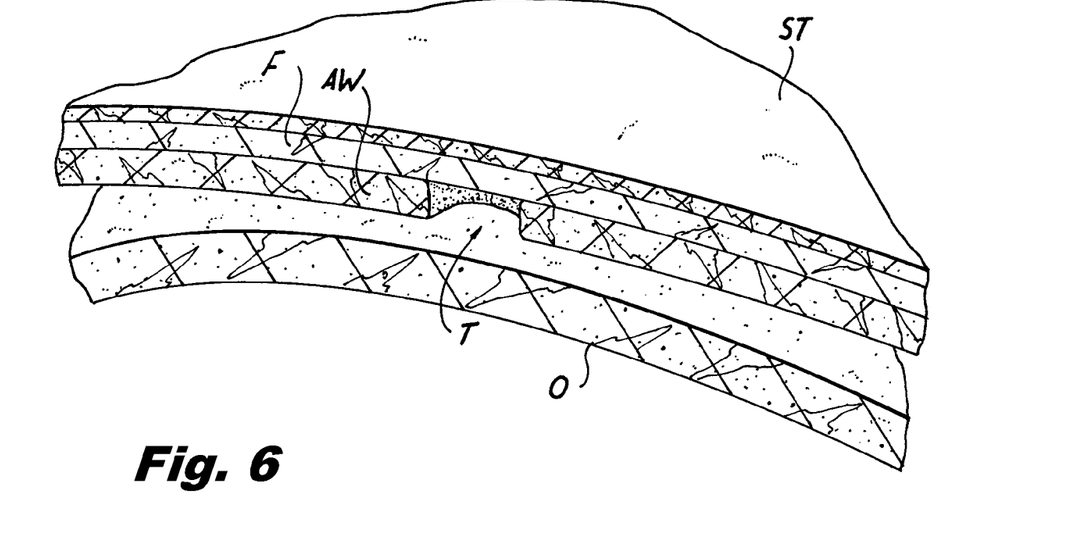
FIG. 6 is a perspective view, partially shown in section, of body wall tissues and underlying organ of a patient.
Figure 7:
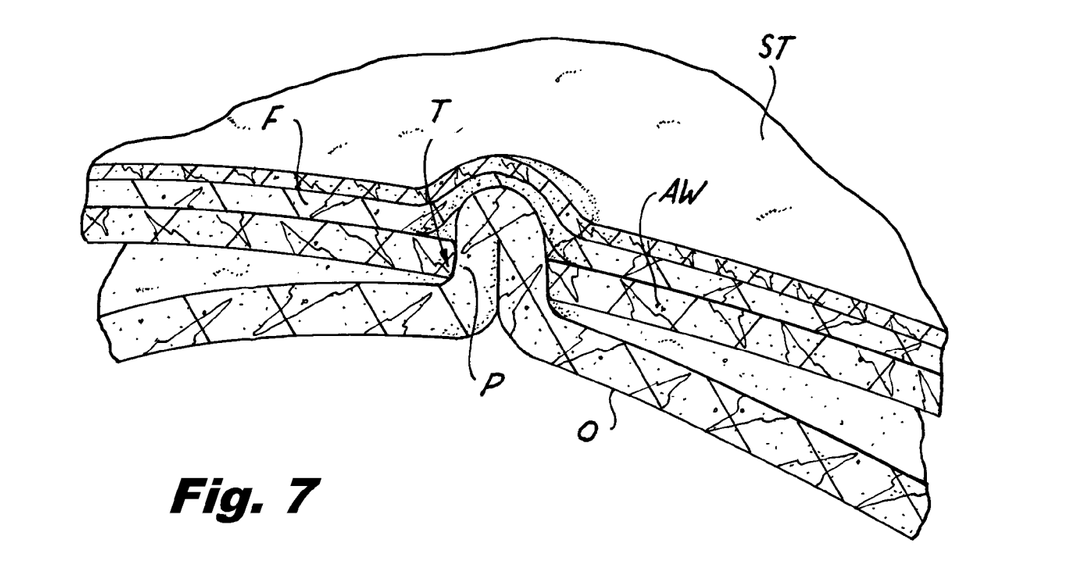
FIG. 7 is a perspective view, partially shown in section, of a portion of the underlying organ encroaching through a tear in an abdominal wall of the body of the patient.

Referring now to FIGS. 6-11, the use of applicator 10 and surgical mesh 12 to repair a tear in tissue will now be described. Referring initially to FIGS. 6 and 7, an opening or tear T often occurs through a body wall, such as, for example, abdominal wall AW exposing overlying airspace or fat F and surface tissue ST through abdominal wall AW (FIG. 6). This allows for a herniated condition to occur where a portion P of an underlying organ O protrudes through tear T and impinges on fat F and surface tissues T resulting in a painful situation for the patient.

Figure 8:
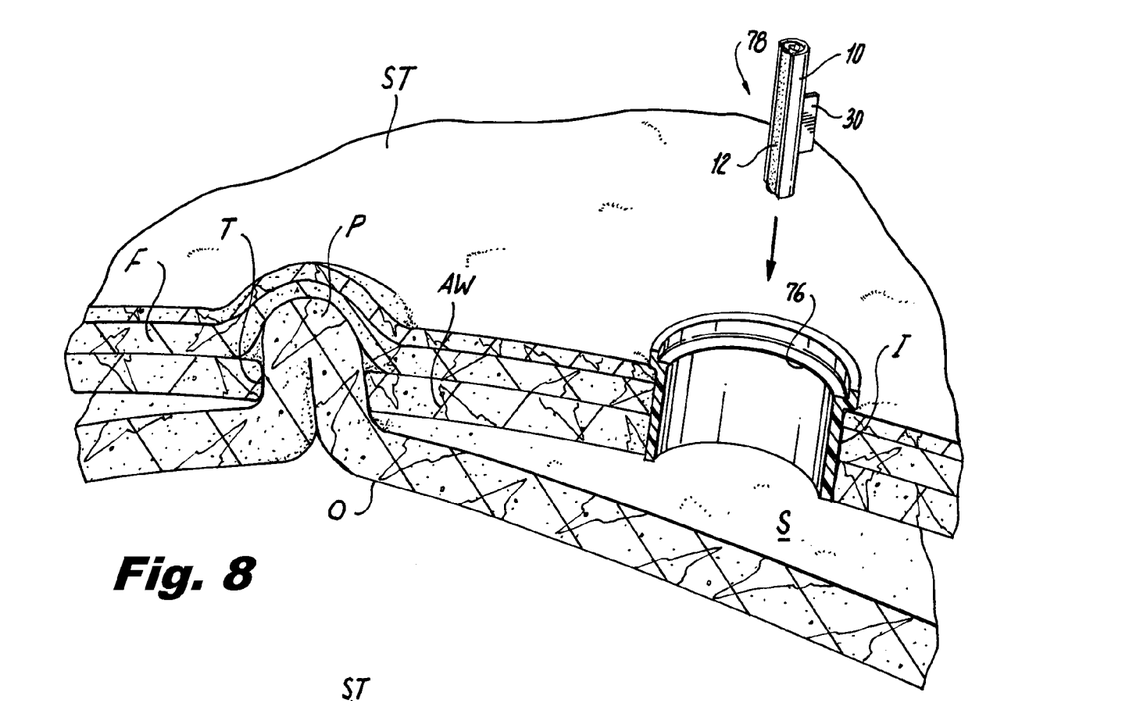
FIG. 8 is a perspective view, partially shown in section, of the applicator and surgical mesh of FIG. 1, being inserted through a port installed through the body wall of the patient.
Figure 9:
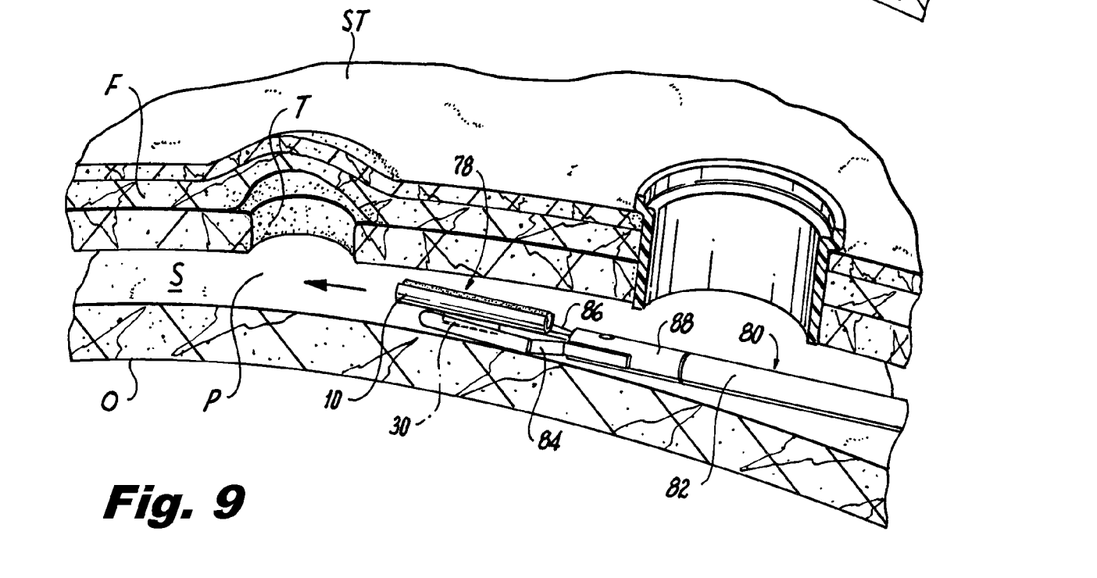
FIG. 9 is a perspective view, partially shown in section, of a grasper advancing the applicator and surgical mesh between the organ and body wall of the patient.

With reference to FIGS. 8 and 9, in order to correct this situation, an access port 74 is inserted through an incision I formed through surface tissue ST, fat F and abdominal wall AW to access a space S between the abdominal wall W and underlying organ O. Space S can be expanded or increased by known methods such as, for example, retraction, insufflation, etc. to create more working room for the surgeon.

Surgical mesh 12 is formed into the roll of mesh material 32 and inserted into chamber 34 of applicator 10 (FIG. 1) to form a surgical repair device 78. Thereafter, surgical repair device 78 is inserted through access port 76 and into space S between abdominal wall AW and organ O.

As best shown in FIG. 9, a surgical grasping instrument 80 is inserted through access port 76 or an auxiliary access port (not shown) to manipulate surgical repair device 78. Surgical grasping device 80 includes an elongate shaft 82 and first and second jaw members, 84 and 86, respectively, pivotally mounted on a distal end 88 of elongate shaft 82. Surgical grasping device 80 is manipulated to grasp surgical repair device 79 and manipulate surgical repair device toward tear T. Specifically, finger grip 30 of applicator 10 is grasped between first and second jaw members 84 and 86 of surgical grasping device 80. Movement of surgical grasping device 80 toward tear T assists to retract portion P of organ O out of tear T.

Figure 10:
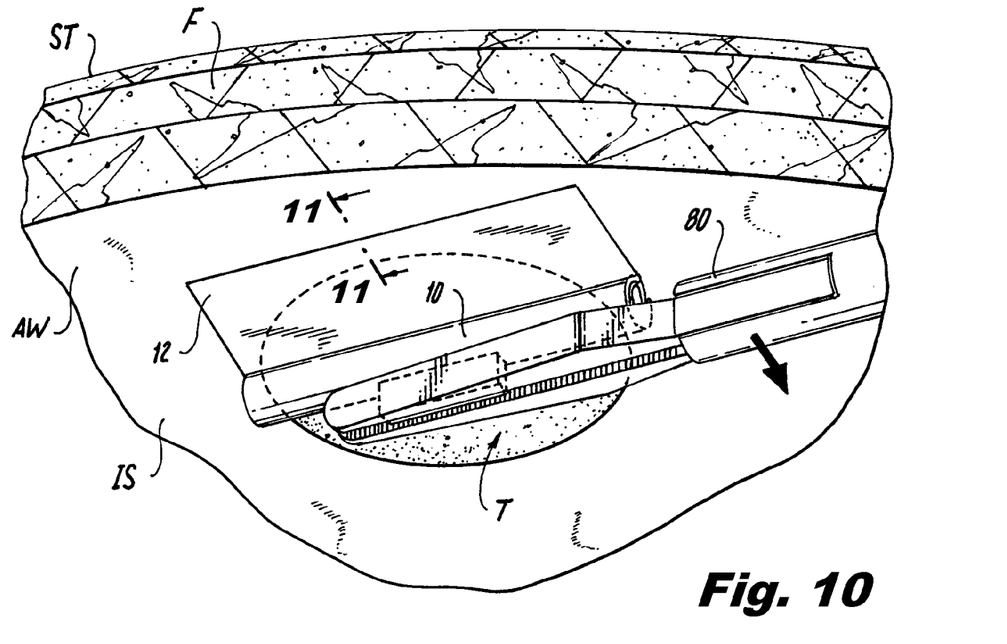
FIG. 10 is a perspective view, partially shown in section, of the applicator being passed over the tear in the abdominal wall to apply the surgical mesh across the tear.

Referring now to FIGS. 1 and 10, surgical grasping device 80 is used to press applicator 10 against abdominal wall AW and move applicator 10 across tear T. As applicator 10 is forced against abdominal wall AW, adhering surface 70 of surgical mesh 12 (FIG. 4), exposed through gap 28 in applicator 10 (FIG. 1), is forced into engagement with abdominal wall AW and adheres to abdominal wall AW as applicator 10 and surgical mesh 12 are passed over tear T, i.e., the roll of mesh material 32 is unrolled against abdominal wall AW and across tear T. Once all of surgical mesh 12 has been applied across tear T, surgical grasping device 80 is use to remove applicator 10 from the operative site.

Figure 11:
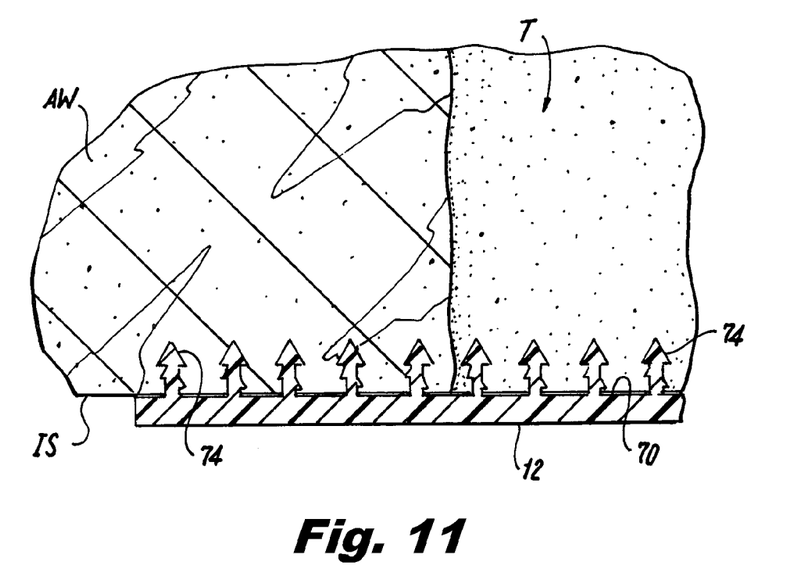
FIG. 11 is a cross-sectional view of the surgical mesh affixed to the abdominal wall and extending across the tear.

As best shown in FIG. 11, barbs 74 extending from adhering surface 70 of surgical mesh 12 engage and penetrate into an inner surface IS of abdominal wall AW to anchor surgical mesh 12 to abdominal wall AW. In this application, barbs 74 extend into tear T as surgical mesh 12 extends across tear T to seal the tear or opening. Alternatively, a surgeon can draw opposed sides of tear T, or other cut or incision, together and use surgical mesh 12 to secure the opposed sides together for sealing the tissue together.

In this manner, surgical repair device 78 is used to repair a tear in tissue to prevent underlying organs from protruding through or across the tear.

Figure 12:
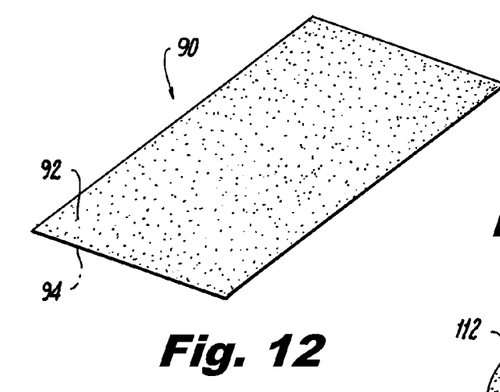
FIG. 12 is a perspective view of one embodiment of a surgical mesh.
Figure 13:
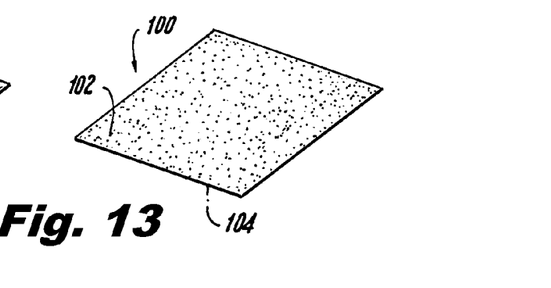
FIG. 13 is a perspective view of an alternative embodiment of a surgical mesh.
Figure 14:
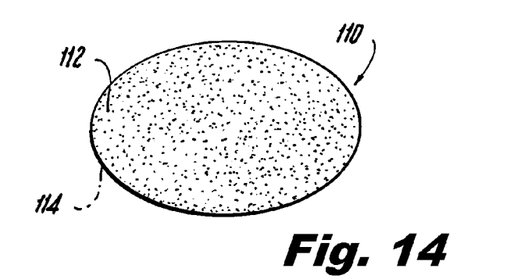
FIG. 14 is a perspective view of a further alternative embodiment of a surgical mesh.

Referring now to FIGS. 12-14, there are disclosed alternative shapes of surgical mesh for use with applicator 10 above. For example, with reference to FIG. 12 there is disclosed a generally rectangular surgical mesh 90 for covering longitudinal tears. Similar to surgical mesh 12 hereinabove, surgical mesh 90 has an adhering surface 92 and a non-adhering surface 94 to prevent self-sticking when rolled and installed within applicator 10. Likewise, FIG. 13 discloses a generally square surgical mesh 100 having an adhering surface 102 and a non-adhering surface 104 and is suitable for use with shorter tears. FIG. 14 discloses a generally round surgical mesh 110 also having an adhering surface for adherence to tissue and a non-adhering surface to prevent self sticking. Surgical mesh 110 is suited for round puncture type wounds to ensure an even amount of securement about the circular edge of the wound or puncture.

It is also within the contemplated scope of the present disclosure that other shapes including, but not limited to, oval, diamond-shaped, polygonal or even asymmetrical shape of surgical mesh, having adhering and non-adhering surfaces may be provided and used with applicator 10 depending on the surgical requirements.

Figure 15:
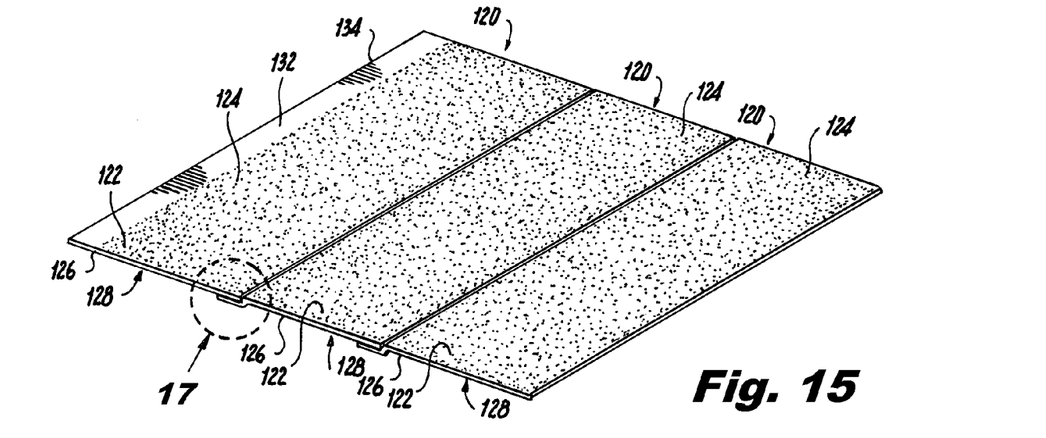
FIG. 15 is a perspective view of a still further alternative embodiment of a surgical mesh applied in overlapping layers.
Figure 16:
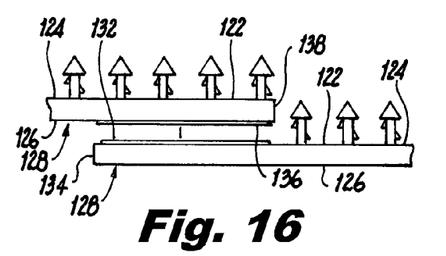
FIG. 16 is a partial end view, with layers separated, of the overlapping surgical mesh embodiment of FIG. 15.
Figure 17:
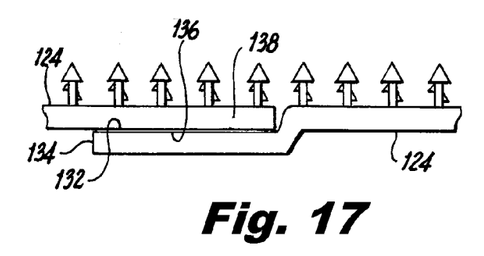
FIG. 17 is enlarged area of detail view taken from FIG. 15.

Referring now to FIGS. 15-17, there is further disclosed a plurality of surgical meshes 120 particularly designed for use in situations requiring overlapping strips of surgical mesh. Each surgical mesh 120 has a predominantly adhering surface 122 on a first side 124 and a predominantly non-adhering surface 126 on a second side 128. Adhering surfaces 122 are provided with tags or barbs 130, similar to barbs 74 described hereinabove, for engaging tissue.

With reference to FIGS. 16 and 17, in order to secure adjacent strips of surgical mesh 120 in overlapping relation relative to a wound or tear, each first side 124 includes a length of adhesive material 132 along one edge 134 and each second side 128 has a corresponding strip or length of adhesive material 136 along an opposing edge 138 for sealing engagement with length of adhesive material 132 on first side 124. Alternatively, second side 128 may be provided with an area (not shown) configured to engage adhering surface 122 of the first side in adhering relation to secure an overlap between adjacent strips of surgical mesh.

It will be understood that various modifications may be made to the embodiments disclosed herein. For example, other adhering structure may be provided on the adhering surface, such as, for example, adhesives, hook and loop fastener portions, etc. Further, the body portion may assume other shapes such as, for example, rectangular, circular, etc. Still further, the grasping structure may include detents or recesses formed in the body portion. Additionally, multiple body portions may be joined together to apply strips of mesh material in overlapping relationship. Therefore, the above description should not be construed as limiting, but merely as exemplifications of particular embodiments. Those skilled in the art will envision other modifications within the scope and spirit of the claims appended hereto.

The invention claimed is:

1. An applicator for applying a surgical mesh to tissue comprising:
a body portion having an inner surface defining a chamber for receipt of a surgical mesh, an outer surface, and first and second longitudinally extending edges, each longitudinally extending edge including an atraumatic, bulbous surface, the first and second longitudinal edges defining a gap therebetween for passage of the surgical mesh.

2. The applicator as recited in claim 1, wherein the body portion is a semi-cylindrical body portion having first and second open ends.

3. The applicator as recited in claim 2, wherein the outer surface includes a gripping structure for manipulating the body portion relative to tissue.

4. The applicator as recited in claim 3, wherein the gripping structure includes a finger grip projecting from the outer surface of the body portion.

5. The applicator as recited in claim 3, further comprising a roller assembly for support of the surgical mesh within the chamber.

6. The applicator as recited in claim 5, wherein the roller assembly includes a first end cap attached to the first open end of the body portion, a second end cap attached to the second open end of the body portion and a shaft extending between the first and second end caps.

7. The applicator as recited in claim 6, wherein a first end of the shaft is affixed to the first end cap and a second end of the shaft is supported within a socket formed in the second end cap.

8. A surgical repair device for applying a surgical mesh to tissue comprising:
a body portion having an inner surface defining a chamber and first and second longitudinal edges, each longitudinal edge including an atraumatic, bulbous surface and defining a gap therebetween; and
a roll of mesh material positioned within the chamber and having a first adhering side and a second non-adhering side.

9. The surgical repair device as recited in claim 8, wherein the roll of mesh material is oriented in a reverse roll with the adhering side facing outward.

10. The surgical repair device as recited in claim 9, wherein the adhering side of the roll of mesh material is exposed through the gap defined by the first and second longitudinal edges.

11. The surgical repair device as recited in claim 8, wherein the adhering side of the roll of mesh material includes tissue engaging barbs for anchoring the mesh to tissue.

12. The surgical repair device as recited in claim 11, wherein the non-adhering side resists puncture from the barbs.

13. The surgical repair device as recited in claim 8, wherein the body portion includes a gripping structure projecting from an outer surface of the body portion.

14. The surgical repair device as recited in claim 8, wherein the body portion is semi-cylindrical.

15. The surgical repair device as recited in claim 8, wherein the roll of mesh material includes a length of adhesive material along an edge of the non-adhering side.

16. The surgical repair device as recited in claim 15, wherein the roll of mesh material includes a length of adhesive material along an edge of the adhering side.

17. A method of applying a surgical mesh to a tear in tissue comprising:
providing a surgical repair device having a body portion defining a chamber and first and second longitudinal edges, each longitudinal edge including an atraumatic, bulbous surface and defining a gap therebetween and a roll of mesh material positioned within the chamber and having a first adhering side exposed through the gap;
exposing the first adhering side of the roll of mesh material to tissue surrounding a tear in the tissue; and
dragging the body portion of the surgical repair device across the tissue surrounding the tear in the tissue to cause the first adhering side of the roll of mesh material to engage the tissue.

18. The method as recited in claim 17, further comprising the step of unrolling the roll of mesh material as the body portion is dragged across the tissue.

19. The method as recited in claim 18, further comprising unrolling a second roll of mesh material such that an edge of the second roll of mesh material overlaps an edge of the unrolled roll of mesh material applied to tissue.

20. The method as recited in claim 19, wherein the edge of the roll of mesh material includes a first adhesive strip and the second roll of mesh material includes an edge having a second adhesive strip which engages the first adhesive strip in overlapping relation.

\* \* \* \* \*